(12) United States Patent
Torp

(10) Patent No.: US 9,687,246 B2
(45) Date of Patent: Jun. 27, 2017

(54) RELEASE MECHANISM

(71) Applicant: COOK MEDICAL TECHNOLOGIES LLC, Bloomington, IN (US)

(72) Inventor: Allan Torp, Bjæverskov (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 240 days.

(21) Appl. No.: 14/515,188

(22) Filed: Oct. 15, 2014

(65) Prior Publication Data
US 2015/0112378 A1    Apr. 23, 2015

(30) Foreign Application Priority Data

Oct. 17, 2013 (GB) .................................. 1318403.1

(51) Int. Cl.
*A61B 17/12* (2006.01)
*A61B 17/00* (2006.01)

(52) U.S. Cl.
CPC .... *A61B 17/12113* (2013.01); *A61B 17/1214* (2013.01); *A61B 17/12022* (2013.01);
(Continued)

(58) Field of Classification Search
CPC ........ A61B 17/12022; A61B 17/12099; A61B 17/12109; A61B 17/12113;
(Continued)

(56) References Cited

U.S. PATENT DOCUMENTS 5,133,727 A * 7/1992 Bales ...................... A61B 17/29
                                                              600/562
5,217,484 A * 6/1993 Marks .............. A61B 17/12022
                                                              128/899
(Continued)

FOREIGN PATENT DOCUMENTS

EP              0428607 A1      5/1991
WO         WO 90/01297         2/1990
(Continued)

OTHER PUBLICATIONS

Henkes, et al. "Endovascular Coil Occulsion of Intracranial Aneurysms Assisted by a Novel Self-Expandable Nitinol Microstent (Nauroform)" Retrieved on May 29, 2013 from http:europepmc.org/articles/PMC3576604/reload=0;jsessionid=GbqFV1ekLKpEuXHbOeJh.4;  p.  108; Interventional Neuroradiology 8: 107-119; 2002.
(Continued)

*Primary Examiner* — Ryan J Severson
(74) *Attorney, Agent, or Firm* — Brinks Gilson & Lione

(57) ABSTRACT

The disclosure provides a release mechanism, method of manufacturing, and method of releasing a medical device. The mechanism comprises a generally elongate shaft, an actuating member receivable in the elongate shaft, the actuating member having an interlocking position and a releasing position, and at least two opposed arms at a distal end of the elongate shaft, biased to open relative to each other, each arm comprising a gripping portion at a distal end, and at least one interlocking member. The gripping portions of the arms may define a hollow space for holding a device. The interlocking member of each arm is longitudinally spaced from the interlocking member of any other arm and extends circumferentially around the actuating member. The actuating member is longitudinally retractable from the interlocking position to the releasing position to enable the arms to open for releasing a medical device from the gripping portions.

18 Claims, 3 Drawing Sheets

(52) U.S. Cl.
CPC ............... *A61B 2017/00526* (2013.01); *A61B 2017/12054* (2013.01); *Y10T 29/49863* (2015.01); *Y10T 29/49996* (2015.01)

(58) Field of Classification Search
CPC ........ A61B 17/12118; A61B 17/12131; A61B 17/1214; A61B 17/12145; A61B 2017/1205; A61B 2017/12054; A61F 2/95; A61F 2/97; A61F 2002/9505
See application file for complete search history.

(56) References Cited

U.S. PATENT DOCUMENTS

| | | | |
|---|---|---|---|
| 5,250,071 A | 10/1993 | Palermo | |
| 5,601,600 A * | 2/1997 | Ton | A61B 17/12022 606/191 |
| 5,722,989 A * | 3/1998 | Fitch | A61B 17/12022 606/205 |
| 5,746,769 A | 5/1998 | Ton et al. | |
| 6,277,125 B1 * | 8/2001 | Barry | A61B 17/12022 606/108 |
| 7,419,498 B2 * | 9/2008 | Opolski | A61B 17/0057 606/215 |
| 7,708,754 B2 * | 5/2010 | Balgobin | A61B 17/12022 606/191 |
| 7,901,444 B2 * | 3/2011 | Slazas | A61B 17/12022 623/1.11 |
| 7,942,894 B2 * | 5/2011 | West | A61B 17/12022 294/99.1 |
| 8,308,789 B2 | 11/2012 | Armstrong | |
| 8,926,650 B2 * | 1/2015 | Que | A61B 17/12022 606/200 |
| 9,307,996 B2 * | 4/2016 | Johnson | A61B 17/12022 |
| 2005/0070758 A1 | 3/2005 | Wells et al. | |
| 2005/0154417 A1 * | 7/2005 | Sepetka | A61B 17/12022 606/200 |
| 2005/0267523 A1 | 12/2005 | Devellian et al. | |
| 2006/0025803 A1 | 2/2006 | Mitelberg et al. | |
| 2006/0074409 A1 * | 4/2006 | Schuermann | A61B 17/221 606/2.5 |
| 2006/0276824 A1 | 12/2006 | Mitelberg et al. | |
| 2007/0179520 A1 | 8/2007 | West | |
| 2007/0186933 A1 | 8/2007 | Domingo et al. | |
| 2007/0203560 A1 | 8/2007 | Forster et al. | |
| 2007/0270930 A1 * | 11/2007 | Schenck | A61B 17/12022 623/1.11 |
| 2007/0282373 A1 | 12/2007 | Ashby et al. | |
| 2007/0293928 A1 | 12/2007 | Tomlin | |
| 2007/0299461 A1 * | 12/2007 | Elliott | A61B 17/12022 606/191 |
| 2008/0045997 A1 | 2/2008 | Balgobin et al. | |
| 2008/0082176 A1 | 4/2008 | Slazas | |
| 2008/0119887 A1 | 5/2008 | Que et al. | |
| 2008/0221654 A1 | 9/2008 | Buiser et al. | |
| 2008/0300616 A1 | 12/2008 | Que et al. | |
| 2009/0036877 A1 | 2/2009 | Nardone et al. | |
| 2009/0099592 A1 | 4/2009 | Buiser et al. | |
| 2009/0270877 A1 | 10/2009 | Johnson et al. | |
| 2011/0054519 A1 * | 3/2011 | Neuss | A61B 17/0057 606/213 |
| 2013/0217956 A1 | 8/2013 | Thompson et al. | |
| 2014/0207175 A1 * | 7/2014 | Aggerholm | A61F 2/01 606/200 |
| 2015/0112378 A1 * | 4/2015 | Torp | A61B 17/12022 606/200 |
| 2016/0157869 A1 * | 6/2016 | Elg rd | A61B 17/12109 606/200 |
| 2016/0302794 A1 * | 10/2016 | Torp | A61B 17/12113 |

FOREIGN PATENT DOCUMENTS

| | | |
|---|---|---|
| WO | WO 00/54662 | 9/2000 |
| WO | WO 2009/014612 B | 12/2009 |

OTHER PUBLICATIONS

Cardinal Search Report dated May 30, 2013.
Great Britain Intellectual Property Office Search Report dated May 14, 2014.
Extended European Search Report for Application No. 14189282.8-1659, dated Mar. 5, 2015 (6 Pages).
European Search Report dated Mar. 5, 2015.

* cited by examiner

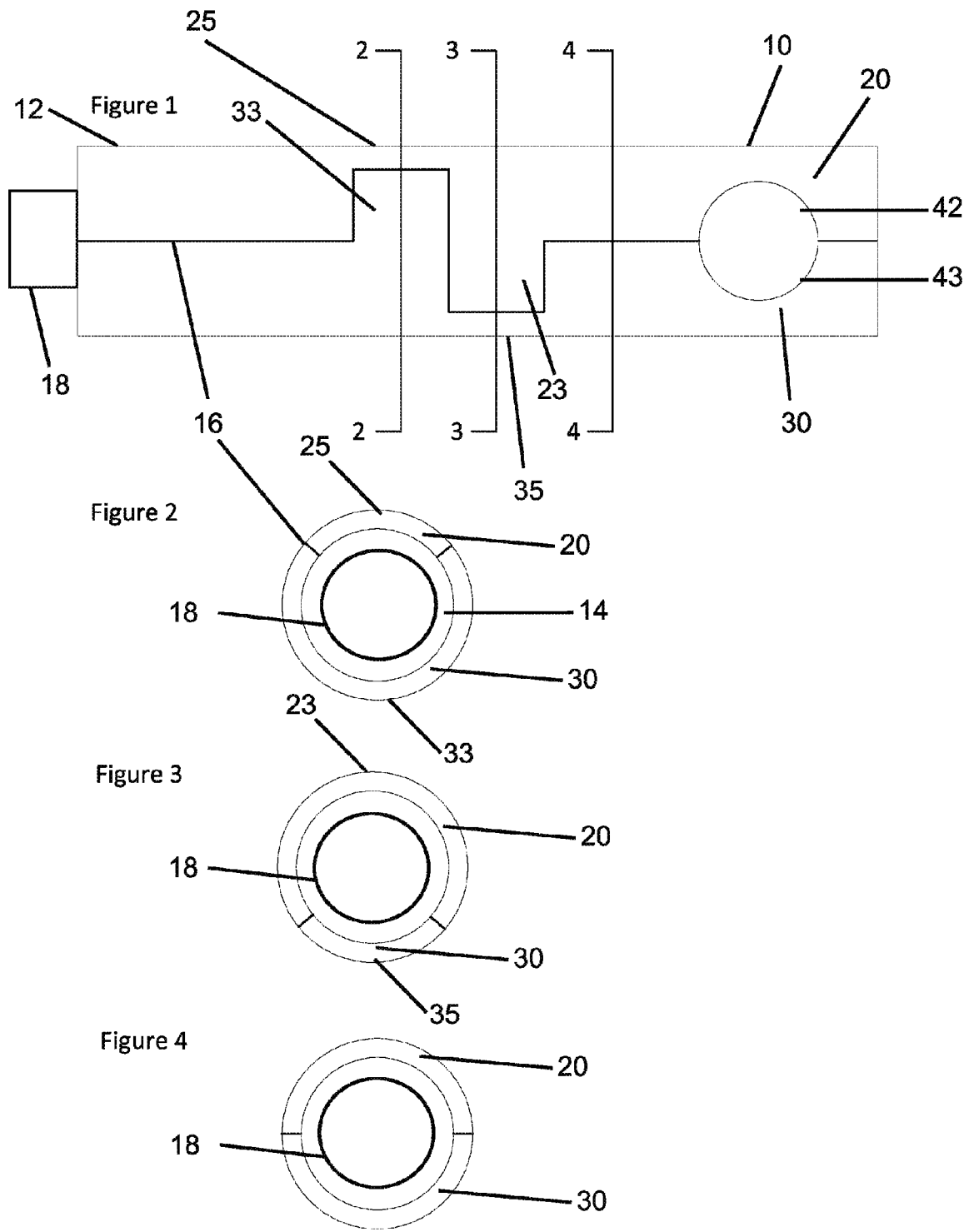

RELEASE MECHANISM

CROSS-REFERENCE TO RELATED APPLICATIONS

This application claims the benefit of priority under 35 U.S.C. §119(a) to Great Britain Patent Application No. 1318403.1, filed Jul. 17, 2013, which is incorporated by reference here in its entirety.

TECHNICAL FIELD

The present invention relates to a mechanism for releasing a medical device, for example a mechanism suitable for holding and releasing an implant, such as an embolic coil, from a medical delivery device for deploying the implant at a selected site. The present invention also relates to a method of manufacturing a release mechanism and to a method of releasing a medical device from a release mechanism.

BACKGROUND ART

Deployment of medical devices such as implants usually requires accurate and reliable placement at a specific site within the vasculature of a patient. For example, an abnormal bulge or aneurysm that may occur in a patient's vessel can be treated by deploying one or more embolic coils into the bulge or aneurysm to occlude the flow of blood into it.

Many different systems and methods have been proposed for delivering such implants, or indeed other medical devices, and most of these involve delivery of the device to the selected site via a catheter and subsequent release or detachment of the implant at the selected site. Some systems, for example, have a mechanism with gripper arms that grip an appropriate feature of the implant (such as enlarged head portion). When the implant is positioned at the selected site, the gripper arms are opened to release it. To ensure effective deployment of the implant once in situ, the gripper arms may be biased open and are therefore constrained into the gripping position during deployment until the implant reaches the desired position. Whilst the prior art systems are generally effective, problems have occurred due to the design of such release mechanisms, particularly in systems where the release mechanism is biased into an open position. In some cases the implant has been released prematurely. This is clearly undesirable as the implant will be incorrectly positioned and must be removed, thus disrupting the medical procedure and potentially risking the health of the patient.

Accordingly there remains a need for an improved release mechanism for releasing a medical device, particularly an implant, at a selected site within the vasculature of a patient, which is reliable and resistant to premature release of the device.

SUMMARY OF THE INVENTION

The present invention seeks to provide an improved release mechanism. From a first broad aspect of the present invention, there is provided a release mechanism for releasing a medical device, the release mechanism comprising: a generally elongate shaft defining a longitudinal axis; an actuating member receivable in the elongate shaft, the actuating member having an interlocking position and a releasing position; and at least two, mutually opposed arms at a distal end of the elongate shaft, the arms being biased to open relative to each other, each arm comprising: a gripping portion at a distal end thereof; and at least one interlocking member, wherein: the gripping portions of the arms at least partially define a hollow space for holding a medical device to be released, the interlocking member of each arm is longitudinally spaced from the interlocking member of any other arm, each interlocking member extends circumferentially around a sufficient proportion of the actuating member such that, when the actuating member is in the interlocking position, opening of the arms is prevented by interaction between the actuating member and the interlocking members, and the actuating member is longitudinally retractable from the interlocking position to the releasing position so as to release the interlocking members and thus enable the arms to open for releasing a medical device from the gripping portions.

The above arrangement provides a simple structure that is easy to form yet that reliably opens when it is desired to deploy a medical device that is gripped by the release mechanism. Furthermore the above arrangement is resistant to premature or otherwise untimely or undesired release of the medical device because the actuating member when in the interlocking position acts as a safety lock and holds the arms together, even against their bias to open, until it is desired to release the device. The actuating member holds the arms because the interlocking member of each arm surrounds a sufficient proportion of the actuating member such that the interlocking member grips the actuating member and cannot be separated from the actuating member unless the actuating member is retracted to its releasing position.

To release the device, opening of the gripping portions is readily achieved simply by retracting the actuating member from interlocking position (i.e. in which it is at least partially surrounded by the interlocking members) to the releasing position, thus releasing the interlocking members and therefore the arms, which then open under their bias to their unrestrained position. This in turn opens the gripping portions and releases the medical device held in the space defined by the gripping portions, deploying the medical device at the appropriate site in the patient. The above arrangement is also very compact and is suitable for low profile systems, particularly as discussed below.

Each interlocking member extends around a sufficient proportion of the actuating member such that, when the actuating member is in the interlocking position, opening of the arms is prevented by interaction between the actuating member and the interlocking members. Namely each interlocking member must surround enough of the circumference of the portion of the actuating member that is in the interlocking member, to prevent the interlocking member from being pulled away from the actuating member (by the bias of its respective arm). The interlocking member may be formed to surround the entire circumference of the portion of the actuating member that is in the interlocking member, i.e. the interlocking member may be in the form of a loop. Alternatively the interlocking member may surround only a portion of the circumference.

The actuating member may be any suitable actuating member for use in a medical procedure and may comprise a substantially cylindrical, elongate member. In this arrangement, each interlocking member will extend around more than 180° of the circumference of this actuating member when the actuating member is in the interlocking position and the arms are closed. The interlocking member of each arm therefore at least partially encircles the actuating member and if there is gap between the end of the interlocking member and any other portion of the release mechanism (e.g. between end portions of the interlocking member), the actuating member is too large to pass through any such gap. Also the interlocking member and relevant other portions of the release mechanism are sufficiently inflexible such that they cannot flex or be deflected sufficiently by pressure from the actuating member (as the arm bias causes the interlocking member to abut the actuating member near any gap) to allow the actuating member to be released through the gap. The actuating mechanism can only be released, and therefore allow the arms to open under their bias, by retracting the actuating member to its releasing position.

It may be desirable to minimise the profile of the release mechanism and this can be achieved by configuring the arms of the mechanism such that there is no significant overlap between portions of one arm with portions of another arm, since overlapping portions increase the thickness (and thus the profile) of the mechanism. Therefore the interlocking member may not entirely surround the actuating member, and thus a gap or spacing is provided at the end of the interlocking member (or between end portions of the interlocking member) that enables a portion of another arm to fit into the gap. Each arm may further comprise a connecting member, the connecting member of a first one of the at least two, mutually opposed arms is located generally opposite the interlocking member of a second one of the at least two, mutually opposed arms, and the connecting member of the second one of the at least two, mutually opposed arms is located generally opposite the interlocking member of the first one of the at least two, mutually opposed arms. Each interlocking member may extend around less than 360° of the circumference of the actuating member, thereby defining a spacing between end portions of the respective interlocking member, the connecting member of the first one of the at least two, mutually opposed arms is interposed between the end portions of the interlocking member of the second one of the at least two, mutually opposed arms, and the connecting member of the second one of the at least two, mutually opposed arms is interposed between the end portions of the interlocking member of the first one of the at least two, mutually opposed arms.

As discussed above, the actuating member is too large to pass through any gap between the end of the interlocking member and any other portion of the release mechanism, etc. By providing the interposed connecting members and interlocking members, sections of one arm can be interposed with sections of another arm, minimising the profile of the mechanism and also enhancing the manufacturability of the mechanism because the interposed sections can be, for example, cut from one material, such as the material forming an elongate shaft, as discussed further below. Each arm may further comprise a recess generally located in the region of the connecting member, the recess for receiving an end portion of the interlocking member of the other arm when the actuating member is in the interlocking position. Namely when the mechanism is in its closed configuration, the interlocking members are interposed between portions of another arm by being received in recesses thereof and the connecting members are also interposed to further maintain the low profile of the mechanism. As before, such an arrangement is suited for formation from an elongate shaft by cutting the various features from a single shaft of material.

Whilst the mechanism may comprise more than two arms, in a particularly useful arrangement the release mechanism may comprises a pair of arms, each arm having a longitudinal axis and, when the actuating member is in the interlocking position, the longitudinal axes of the arms are substantially parallel to each other. In some arrangements, for example, the release mechanism may comprise an upper arm and a lower arm. When the actuating member is in the interlocking position and the arms are closed, the upper arm is substantially parallel to the lower arm, the interlocking member of the upper arm extending at least partially beneath the actuating member, and the interlocking member of the lower arm extending at least partially above the actuating member. Namely the interlocking member of the upper arm extends from above the actuating member (where the arm is located), down and around the actuating member and at least partially beneath it, so that by encircling a substantial and effective part of the circumference of the actuating member, separation of the interlocking member from the actuating member is prevented. Similarly, the interlocking member of the lower arm extends from beneath the actuating member (where the arm is located), up and around the actuating member and at least partially above it, to encircle a substantial and effective part of the circumference of the actuating member.

The interlocking members of the arms may extend around a proportion of the actuating member as discussed above in the various arrangements. Additionally or alternatively each interlocking member may (further) comprise a strip joined at least at one end and preferably at either end of the strip to the respective arm and depending therefrom in the general direction of an opposing arm wherein each strip and respective arm together extend circumferentially around the actuating member to prevent opening of the arms. This arrangement also provides a simple structure that is easy to form yet that reliably opens when it is desired to deploy a medical device that is gripped by the release mechanism. The actuating member holds the strips against the bias of the arms to open because it passes through a lumen defined by the depending strips and their associated arm and thus the arms are held in place (i.e. in the closed position) by the actuating member. To release the medical device, opening of the gripping portions is easily achieved simply by retracting the actuating member from the interlocking position to the releasing position thus releasing the strips and thereby releasing the arms, which then open under their bias to their unrestrained position. This in turn opens up the gripping portions and releases the medical device. Such an arrangement is very secure as the actuating member is at least partially and may be entirely encircled by the strip in co-operation with the arm from which it depends, but is easily released by retraction of the actuating member to the releasing position.

The strips and/or arms from which they depend, can be of any suitable configuration. For certain actuating members, for example an elongate member such as a wire, each arm may have a generally arcuate inner surface, and each strip may be generally arcuate such that the arcuate strip and respective arm together at least partially, and preferably entirely, encircle the actuating member when the actuating member is in the interlocking position. This configuration may aid in insertion and retraction of the actuating member and also may have a shape and preferably a size that is similar to the shape of the actuating member, which may further improve the operation of the mechanism. Still further, such an arrangement again lends itself well to manufacturing of a release mechanism from a member such as a tubular member by cutting or the like. Each strip may be integrally formed with a respective arm, for example by use of (e.g. laser) cutting. Each strip may be defined by a pair of circumferential slits in a generally concave portion of the respective arm, the strip between the pair of circumferential slits being deflected inwardly in the general direction of an opposing arm, preferably by pressing on the strips, to form a generally convex arcuate strip. Thus a simple to manufacture mechanism is provided that reliably remains in a closed configuration until moved into a desired position in a patient and that is easily released simply by retracting the actuating member.

The material from which the strips are formed may be sufficiently resilient that the strips return to their undeflected position when any deflecting force is removed, and are only retained in that position by the actuating member. However for ease of use, the arms may be formed from a material such that the strips remain in the inwardly deflected position after being deflected. This may be preferable where the actuating member will not be inserted into the elongate shaft and/or into its interlocking position immediately and, for example, may instead be inserted at a later stage, possibly just prior to deployment of the release mechanism and associated medical device held within it.

As discussed above, the release mechanism may comprise at least two arms each comprising at least one strip. When deflected inwardly, the strips define parts of a lumen through which the actuating member is moveable from its interlocking position to its releasing position. Therefore the strips cannot be completely aligned in the longitudinal direction of the mechanism as they would interfere with each other and no lumen would be defined. Whilst the strip of one arm may be closely located to the strip of another arm, indeed they could be immediately adjacent each other and abutting, it may be preferable for them to be spaced apart to a greater degree. Spacing the strips apart may give more structural rigidity to the mechanism, particularly if the material forming the arms is very thin, flexible or soft. This may be helpful when advancing the mechanism through the patient's vessels. Therefore the strip of a first one of the at least two, mutually opposed arms may be spaced apart in the longitudinal direction from the strip of a second one of the at least two, mutually opposed arms by between about 0.01 mm and 10 mm, preferably between about 0.05 mm and 5 mm, preferably between about 0.1 mm and 1 mm, preferably between about 0.1 mm and 0.5 mm.

As discussed above, the release mechanism is particularly suitable for low profile applications and procedures. This is enhanced because the inward deflection of the strips of these arrangements provides a secure locking mechanism (in conjunction with the actuating member) without any increase to the outer diameter of the mechanism. Namely the largest diameter of the mechanism can be defined by the outer diameter of the elongate shaft. The outer diameter of the release mechanism (e.g. the outer diameter of the elongate shaft) in any arrangement in accordance with the present invention may be less than about 0.50 mm (0.020 inches), or may be less than about 0.36 mm (0.014 inches). The possible low profile of the mechanism renders it suitable for many medical applications which may be constrained by the dimensions of, for example, the vasculature of the patient.

In any of the above arrangements, the elongate shaft and/or the arms may be formed of any suitable material. The material may be relatively rigid or may be flexible. The arms and/or the elongate shaft may be flexible, preferably being formed from a flexible material, preferably comprising a flexible polymeric material, preferably polyimide elongate shaft and/or the arms may be formed from a flexible material. The arms and/or the elongate shaft may comprise a metal alloy, and may comprise or be formed from a flexible metal alloy. Suitable materials include, for example, Nitinol, polymeric materials, e.g. polyimide, steel, or the like. Nitinol is useful particularly for the arms because shape memory materials such as Nitinol can be formed to provide the bias for the arms to open. Alternatively, flexible polymeric materials such as polyimide are particularly useful because the rolled shape of the mechanism is biased to unroll unless held in the rolled configuration.

Whilst any suitable number of arms may be provided in accordance with the present invention, the mechanism may comprise two mutually opposed arms, the arms being substantially parallel to each other when held against their bias by the actuating member (as discussed with regard to some arrangements above). Namely a pair of opposed parallel arms may be provided which open by deflecting or separating away from each other and/or tilting and/or bending relative to each other or the like. A pair of arms is beneficial to the simplicity and formation of the device.

The elongate shaft may be separately formed from the arms and these components attached together in a suitable manner, with the arms being attached to the distal end of the elongate shaft. This is useful for adding a release mechanism to an existing catheter, for example. Alternatively the arms may be integrally formed from or with the elongate shaft. This enables the shaft and arms to be, for example, moulded or otherwise formed from the same material which may be preferred for manufacturing ease and also provides a more resilient device that may be less prone to separation of the components. The arms may be formed by cutting suitable shapes from the distal end of an elongate shaft, preferably by laser cutting or the like. The elongate shaft and the arms may be integrally formed as a part of a distal end of a catheter. Alternatively the elongate shaft and arms of the mechanism may be integrally formed and be configured to be suitable for insertion into, over or through a catheter.

Similarly the gripping portions may be separately provided from, and attached to, the arms to form the complete arms, but for ease of manufacture and reliability of the device, the gripping portions may be integrally formed with or from the arms. For example the gripping portions may be moulded at the same time as the arms or may be cut, for example laser cut, from the distal ends of the arms.

The actuating member may comprise any suitable member and may comprise a wire, the wire being of a suitable length and diameter for receiving in the elongate shaft and in the interlocking position. The wire may be of sufficient length to extend entirely through the elongate shaft, the wire being retractable from a proximal end thereof to release the arms. Thus easy removal of the actuating wire is provided as it can simply be pulled through the elongate shaft (and indeed through any catheter to which the elongate shaft is attached or is inserted or is formed with) from a proximal end to release the medical device.

The wire may be a thin wire (i.e. having a very small diameter) for ease of manipulation. Alternatively or additionally the wire may be configured so as to fit closely inside the elongate shaft inner lumen (or the lumen partially defined by the strips (where present) as discussed above), thus providing some friction between the wire and the material of the elongate shaft/strips, maintaining the relative positioning between the two until the friction is overcome (for example by pulling sufficiently hard on the end of the wire to withdraw it). Therefore the wire may have an outer diameter substantially similar to the inner diameter of the elongate shaft for a close fit.

The low profile of the mechanism in the various arrangements can be further enhanced by ensuring that no portion of the mechanism extends beyond the outer periphery defined by the diameter of the elongate shaft (the dimension of the length of the mechanism probably not being of such great concern). The gripping portions of the arms may define the distal end of the release mechanism and preferably have a dimension that is less than the outer diameter of the elongate shaft so as not to increase the outer profile of the release mechanism when opening of the arms is prevented. The outer profile of the mechanism may increase once the arms are free to open under their bias, but this will only be when the mechanism is at the appropriate site for deploying the medical device, not as it is moving through the vessels or the like of the patient.

The gripping portions at the distal ends of the arms define a space in which a medical device can be held when the arms are in their closed position (i.e. held by the actuating member against their bias for opening). The space can be any suitable shape and size for holding any device that it may be desired to deploy into a patient. In an example where the object is an embolic coil, the coil may have a suitably shaped end portion to enable it to be gripped. Therefore the hollow space at least partially defined by the gripping portions may be configured for holding an embolic coil. The embolic coil may have an enlarged head portion at a proximal end thereof, and the head portion may be, for example, substantially spherical. Thus the hollow space may be substantially spherical or the gripping portions may at least partially define a spherical hollow space, for securely receiving the head portion of the embolic coil. However when the arms are unlocked by retracting the actuating member to its releasing position, the hollow space is enlarged as the gripping portions open relative to one another and the head of the coil is released. Thus there is provided a simple, reliable and low profile mechanism for releasing an embolic coil that is also resistant to any premature or otherwise unwanted release of the coil until it is in the desired location.

The gripping portion of each arm is not necessarily the same as the gripping portion(s) of other arm(s). For example, one gripping portion may define a cup shape to receive at least a part of a medical device and another gripping portion may define a surface to abut the part of the medical device and enclose it in the cup. However the gripping portion of a first one of the at least two, mutually opposed arms may be substantially similar in shape and size to the gripping portion of a second one of the at least two, mutually opposed arms. This provides a reliable release mechanism that is easy to manufacture and also its symmetry in this regard means that operation of the mechanism will not be determined by, for example, the orientation of the mechanism, as it might be for non-symmetrically similar gripping portions.

From a further broad aspect of the present invention, there is provided a method of manufacturing a release mechanism for releasing a medical device, the method comprising: forming an elongate shaft that defines a longitudinal axis; and cutting at least two, mutually opposed arms at a distal end thereof such that the arms are biased to open when unconstrained, each arm having at least one interlocking member and a gripping portion, the gripping portion located at the distal end of the arm, wherein: the interlocking member of each arm is longitudinally spaced from the interlocking member of any other arm, the gripping portions are formed so as to at least partially define a hollow space for holding a medical device to be released, and the interlocking members are formed such that each interlocking member extends around a sufficient proportion of an actuating member when the actuating member is in an interlocking position such that opening of the arms is prevented by interaction between the actuating member and the interlocking members.

The above method is a simple way to manufacture a low profile release mechanism that may be formed from a single component yet is suitable for reliably deploying a medical device and is resistant to premature release of the device. The method may further comprise cutting the arms so as to define at least one recess in each arm, the recess for receiving at least a part of an interlocking member of another arm. This provides a compact arrangement that also minimises the amount of material in the release mechanism making the mechanism lighter and more flexible.

The method may further comprise: cutting a first pair of circumferential slits into a first one of the at least two mutually opposed arms to define a first strip; cutting a first pair of circumferential slits into a first one of the at least two mutually opposed arms to define a first strip; cutting a pair of circumferential slits into a second one of the at least two mutually opposed arms to define a second strip, the second strip being longitudinally spaced from the first strip; and pressing the first and second strips inwardly in the general direction of an opposing arm to form arcuate strips. Thus the advantageous strips of the above release mechanisms can be provided.

The method may further comprise introducing an actuating member, preferably comprising an actuating wire, into the lumen defined by each arcuate strip and the respective arm from which it is cut, thereby holding the arms against their bias to open.

From a further broad aspect of the present invention, there is provided a method of releasing a medical device from a release mechanism, comprising: positioning a release mechanism in a location where it is desired to release a medical device that is gripped by the release mechanism, the release mechanism comprising: a generally elongate shaft defining a longitudinal axis; and at least two, mutually opposed arms at a distal end of the elongate shaft, the arms being biased to open relative to each other and each comprising a gripping portion at a distal end thereof and at least one interlocking member, the interlocking member of each arm being longitudinally spaced from the interlocking member of any other arm, retracting an actuating member from a proximal end of the elongate shaft, the actuating member thereby moving from an interlocking position, in which the interlocking members extend circumferentially around a sufficient proportion of the actuating member to prevent opening of the arms, to a releasing position so as to release the interlocking members, thus opening the arms under their bias and releasing a medical device from the gripping portions of the arms at the desired location. Therefore there is provided an advantageous method for deploying a medical device at a desired location that is simple and reliable to affect and minimises the risk of early release of the medical device.

The invention extends to methods and/or mechanisms substantially as herein described with reference to the accompanying drawings.

Any apparatus feature as described herein may also be provided as a method feature, and vice versa. As used herein, means plus function features may be expressed alternatively in terms of their corresponding structure.

Any feature in one aspect of the invention may be applied to other aspects of the invention, in any appropriate combination. In particular, method aspects may be applied to apparatus aspects, and vice versa. Furthermore, any, some and/or all features in one aspect can be applied to any, some and/or all features in any other aspect, in any appropriate combination.

It should also be appreciated that particular combinations of the various features described and defined in any aspects of the invention can be implemented and/or supplied and/or used independently.

BRIEF DESCRIPTION OF THE DRAWINGS

These and other aspects of the present invention will become apparent from the following exemplary embodiments that are described with reference to the following figures, in which:

FIG. 1 is a schematic view of a release mechanism in accordance with embodiments of the present invention, illustrating how the mechanism may be formed from a tubular structure;

FIG. 2 is a schematic view of a section of the mechanism of FIG. 1 through line 2-2 of FIG. 1;

FIG. 3 is a schematic view of a section of the mechanism of FIG. 1 through line 3-3 of FIG. 1;

FIG. 4 is a schematic view of a section of the mechanism of FIG. 1 through line 4-4 of FIG. 1;

DESCRIPTION OF THE PREFERRED EMBODIMENTS

Figure 5:
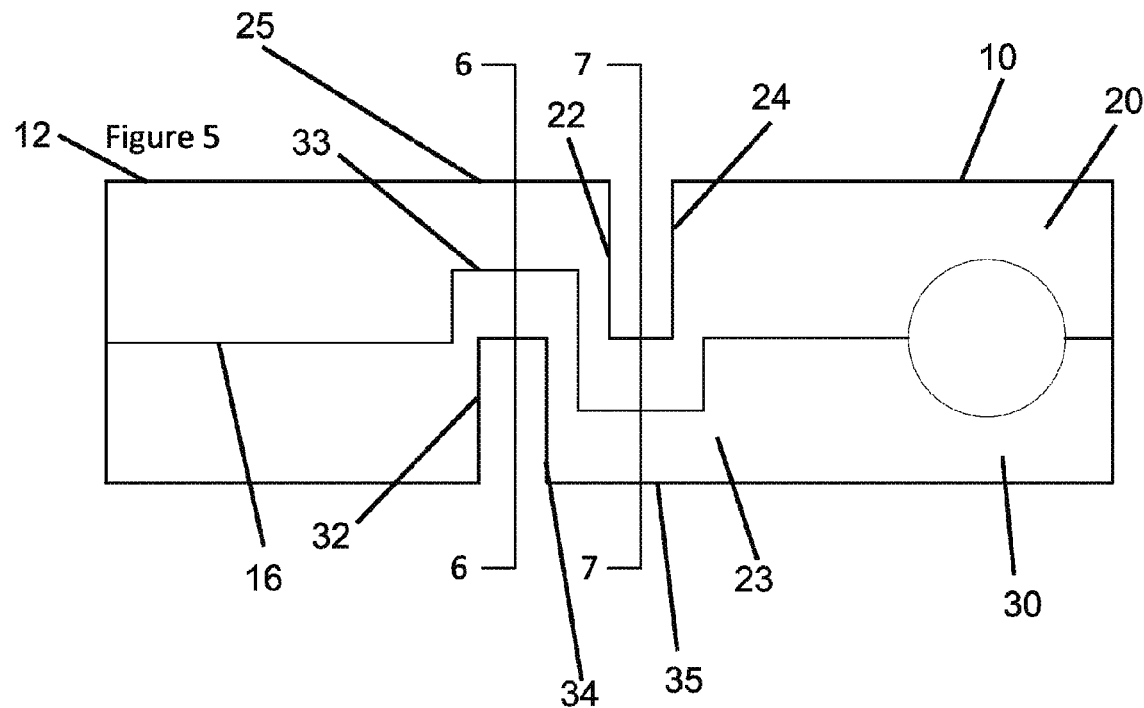
FIG. 5 is a schematic view of a release mechanism in accordance with alternative embodiments of the present invention, illustrating how the mechanism may be formed from a tubular structure and with arcuate strips.

It is to be understood that the Figures are schematic and do not necessarily show the various aspects of the embodiments of the present invention to scale. References to features being relative to another feature or the like are not intended to be limiting and are for ease of understanding. For example references to anything being 'proximal' or 'distal' are not intended to be limiting except insofar as they describe the relationships between various aspects of the embodiments. In the present specification, proximal is used to describe anything that is at the end closest to the practitioner carrying out the procedure and distal is used to describe anything that is at the end furthest from the practitioner carrying out the procedure.

FIG. 1 schematically illustrates a release mechanism 10 in accordance with the present invention. The mechanism comprises an elongate shaft 12 having an inner lumen 14 passing through it. An actuating member such as a wire 18 can pass through the lumen and be positioned to maintain the mechanism 10 in its closed configuration (as shown) and can be retracted from this interlocking position to a releasing position to enable the mechanism 10 to release a medical device as discussed below.

Integrally formed with the shaft 12, by cutting suitable shapes from the shaft 12, are a pair of arms 20, 30. In this example the arms 20, 30 and shaft 12 are formed from the same flexible tube by laser cutting suitable shapes from the tube along cut line 16. FIG. 1 shows the front side of the mechanism 10 and the rear side of the mechanism has the same cut line 16, as can be appreciated from FIGS. 2 to 4 that show the mechanism 10 of FIG. 1 in cross-section. The cut or slit 16 allows the arms 20, 30 to open such that gripping portions 42, 43 at the distal ends of the arms 20, 30 (which in this example are also laser cut from the same tube) open to release a medical device (not shown). The arms 20, 30 are mutually opposed and are substantially parallel when in this closed configuration as can be seen in FIG. 1. Though not depicted, the arms are biased to open and when free to do so will separate away from each other, opening up the gripping portions 42, 43.

Each arm 20, 30 has a respective interlocking member 23, 33 and a respective connecting member 25, 35. These are each formed by the cutting the tube and are interposed with each other to form a very compact and low profile mechanism 10. As can be seen in FIG. 2, the upper arm 20 has a connecting portion 25 located at section 2-2, above and interposed between the outermost tips of the interconnecting member 23 of the lower arm 30. The connecting portion 25 connects the interlocking member 23 of the upper arm 20 to the shaft portion 12 and the connecting portion 35 of the lower arm 30 connects the interlocking member 33 to the gripping portion 43 of the lower arm 30. Each connecting portion 25, 35 opposes the interlocking member 33, 23 of the other arm 30, 20 and defines a recess into which the interlocking member 33, 23 is received.

As can be seen from FIG. 2, at this section along the length of the mechanism 10, the interlocking member 33 of the lower arm 30 forms more than half of the inner shaft lumen 14. When an actuating member (not shown), such as a wire, is received in the lumen 14, movement of the lower arm 30 in the direction of its bias (i.e. downwards in FIGS. 1 to 4) is prevented because the interlocking member 33 surrounds more than half of the wire and the spacing between the end portions of the interlocking member 33 is too small for the wire to pass through (and there is insufficient flexibility in the end portions of the interlocking member 33 to allow them to be deflected apart for the wire to pass through them). Thus downward movement of the lower arm 30 is prevented for as long as the wire is in place in the lumen 14, by this section of the mechanism 10.

Similarly, and as can be seen from FIG. 3, at this section along the length of the mechanism 10, the interlocking member 23 of the upper arm 20 forms more than half of the inner shaft lumen 14. When the wire is received in the lumen 14, movement of the upper arm 20 in the direction of its bias (i.e. upwards in FIGS. 1 to 4) is prevented because the interlocking member 23 surrounds more than half of the wire and the spacing between the ends of the interlocking member 23 is too small for the wire to pass through (and there is insufficient flexibility in the ends of the interlocking member 23 to allow them to be deflected apart for the wire to pass through them). Thus upward movement of the upper arm 20 is prevented for as long as the wire is in place in the lumen 14, by this section of the mechanism 10.

As shown in FIG. 4, at this section along the mechanism 10, the arms are substantially the same and are mirror images of each other and neither arm 20, sufficiently encircles the wire to prevent movement of the arm 20, 30 in the direction of its bias.

Therefore each arm 20, 30 is prevented at a particular section along the mechanism 10 from opening by the interaction of the interlocking portion 23, 33 of the arm 20, 30 with the wire. The upper arm 20 interlocking portion 23 interacts with the wire at one location along the length of the mechanism 10 and the lower arm 30 interlocking portion 22 interacts with the wire at another, longitudinally spaced location along the length of the mechanism 10, enabling the mechanism 10 to be formed from a single strip of tubular material and providing a compact and low profile mechanism 10. Once the wire is removed, it can readily be seen from FIGS. 2, 3 and 4 that the arms 20, 30 are free to move apart under their bias.

FIG. 5 illustrates an alternative release mechanism 10 in accordance with the present invention. The mechanism comprises an elongate shaft 12 having an inner lumen 14 passing through it, the same as the arrangement of FIG. 1. Indeed the release mechanism 10 of FIG. 5 is the same as the release mechanism of FIG. 1 but the interlocking members of the FIG. 5 arrangement are further provided with arcuate strips 26, 36. These strips 26, 36 are also integrally formed with the shaft 12, by cutting a pair of circumferential strips 22, 24 from the interlocking member 23 of the first arm 20 and a pair of circumferential strips 32, 34 from the interlocking member 33 of the second arm 30. The slits 22, 24, 32, 34 of each pair are substantially parallel to each other and are substantially perpendicular to the longitudinal axis of the elongate shaft 12. In the example shown in FIG. 5, the slits 22, 24, 32, 34 when viewed from the end of the mechanism 10 have a substantially semi-circular or arcuate shape, although they may cover more or less of the surface of each arm 20, 30 in other arrangements.

The slits 22, 24, 32, 34 define the deflectable strips 26, 36 of the interlocking members 23, 33 of the arms 20, 30. Each deflectable strip 26, 36 is pushed inwardly (i.e. in the direction towards the opposing arm 20, 30 and towards the centre of the lumen 14). The strips 26, 36 are shown fully deflected in FIGS. 5 to 7, with the strip 36 of the second arm 30 being seen in FIG. 6 and the strip 26 of the first arm 20 being seen in FIG. 7. In this arrangement, once deflected the strips 26, 36 remain in their inwardly deflected position even after removing the pressing force.

Figure 6:
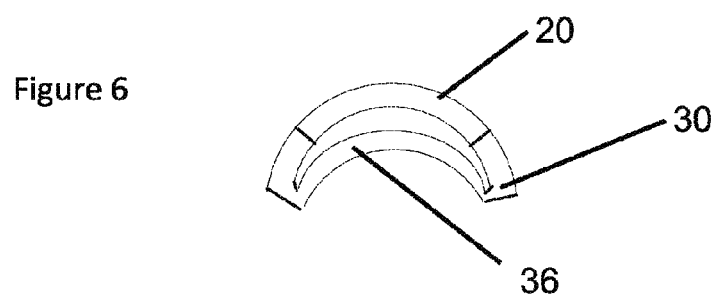
FIG. 6 is a schematic view of a section of the mechanism of FIG. 5 through line 6-6 of FIG. 5.
Figure 7:
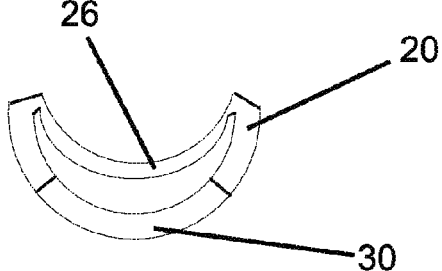
FIG. 7 is a schematic view of a section of the mechanism of FIG. 5 through line 7-7 of FIG. 5.
Figure 8:
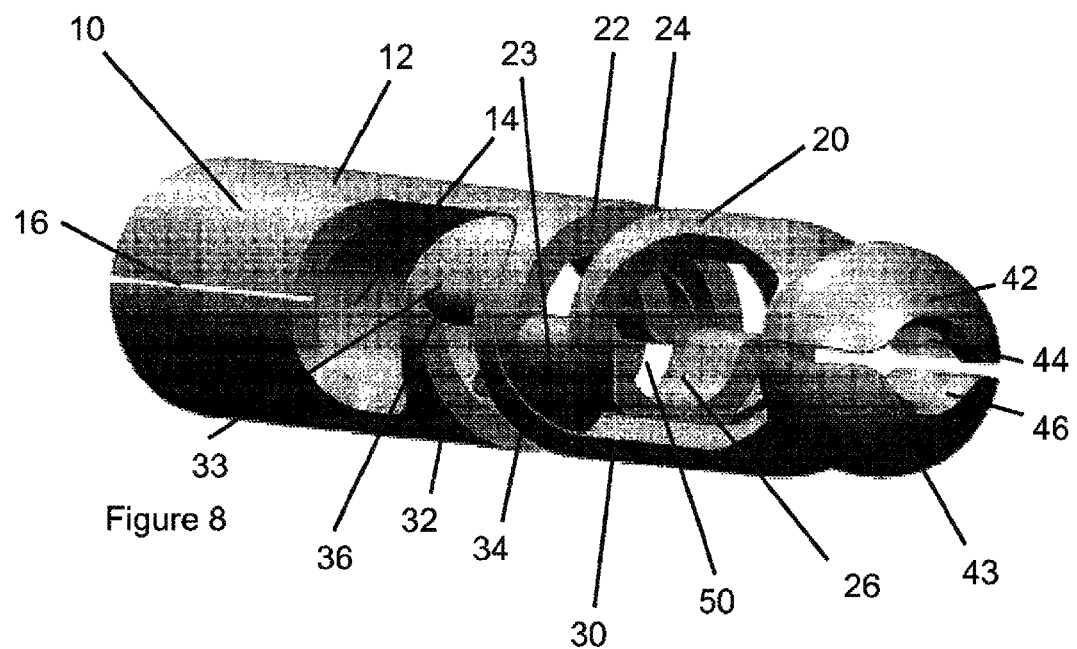
FIG. 8 is a front perspective view of a release mechanism in accordance with embodiments of the present invention.
Figure 9:
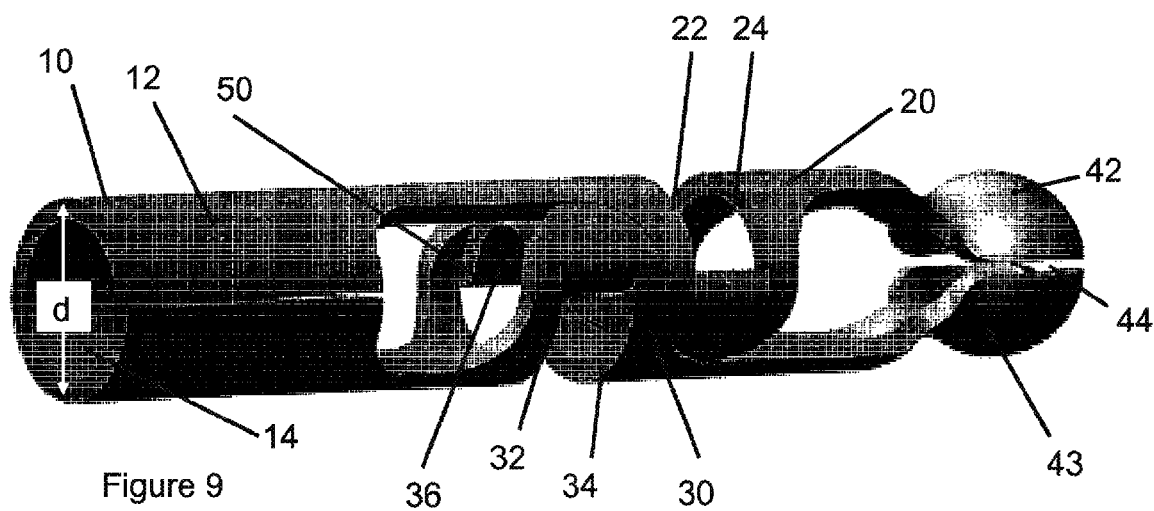
FIG. 9 is an alternative perspective view of the release mechanism of FIG. 1 showing the opening at the proximal end of the elongate shaft.

The deflected strips 26, 36 partially define an actuator lumen 50, which can be seen in the arrangement of FIGS. 8 and 9 (to which the arrangement of FIGS. 5 to 7 is similar). The actuator lumen 50 is within the inner shaft lumen 14 that extends along the length of the mechanism 10. The strips 26, 36 clearly only define parts of the walls of the lumen 50, with an upper partial wall segment being defined by the upper strip 26 and a lower partial wall segment being defined by the lower strip 36. However these partial segments are sufficient for an actuating member 18 (not shown) when introduced into the actuator lumen 50 to abut against the strips 26, 36 (under the biasing of the arms 20, 30) and to oppose their opening. In other words, upper arm 20 is biased upwardly but is prevented from moving upward by abutment of the upper strip 26 on the underside of the actuating member 18 and lower arm 30 is biased downwardly but is prevented from moving downward by abutment of the lower strip 36 on the topside of the actuating member 18. The actuating member 18 obstructs and prevents movement of the strips 26, 36 of the interlocking members 23, 33 thus preventing movement of the arms 20, 30 and likewise preventing the gripping portions 42, 43 opening to release a device held between them.

As best seen in FIGS. 8 and 9, which show a mechanism 10 similar to the schematically shown mechanism of FIGS. 5 to 7, gripping portions 42, 43 of the arms 20, 30 at least partially define a hollow spherical space 44 and an opening orifice 46 for holding an object to be released. In particular, this arrangement is suitable for holding an embolic coil (not shown) having an enlarged head portion at its proximal end, typically a ball. The ball is held in the spherical space 44 and the orifice 46, through which the coil protrudes from the mechanism 10, is too small for the ball to pass through. However when the actuating member (not shown in this Figure) is moved to its releasing position the strips 26, 36 are released and the biased open arms 20, 30 open and thus also enlarge the orifice 46 and release the ball from the spherical space 44. The medical device is thus deployed.

As can be seen in FIG. 9, this mechanism 10 is particularly suited to use for procedures where space and size are constrained, as the profile of the mechanism 10 is defined by the diameter d of the shaft portion 12.

Whilst the arrangement of FIGS. 5 to 7 and 8 and 9 illustrate mechanisms 10 having interlocking members 23, 33 that surround more than half of the wire at portions along the length of the mechanism 10 (as also in accordance with FIGS. 1 to 4) and additionally strips 26, 36, it is within the scope of the invention for the interlocking members 23, 33 to comprise just the strips 26, 36 and it is not necessary for the interlocking members 23, 33 to also surround more than half of the wire if the strips 26, 36 are present.

The invention claimed is:

1. A release mechanism for releasing a medical device, the release mechanism comprising:
   a generally elongate shaft defining a longitudinal axis;
   an actuating member receivable in the elongate shaft, the actuating member having an interlocking position and a releasing position; and
   at least two, mutually opposed arms at a distal end of the elongate shaft, the arms being biased to open relative to each other, each arm comprising:
      a gripping portion at a distal end thereof;
      at least one interlocking member, wherein the gripping portions of the arms at least partially define a hollow space for holding a medical device to be released, the interlocking member of each arm is longitudinally spaced from the interlocking member of any other arm, each interlocking member extends circumferentially around a sufficient proportion of the actuating member such that, when the actuating member is in the interlocking position, opening of the arms is prevented by interaction between the actuating member and the interlocking members, and the actuating member is longitudinally retractable from the interlocking position to the releasing position to enable the arms to open for releasing a medical device from the gripping portions; and
      a connecting member, the connecting member of a first one of the at least two, mutually opposed arms is located generally opposite the interlocking member of a second one of the at least two, mutually opposed arms, and the connecting member of the second one of the at least two, mutually opposed arms is located generally opposite the interlocking member of the first one of the at least two, mutually opposed arms;
   wherein each interlocking member defines a spacing between end portions of the respective interlocking member, the connecting member of the first one of the at least two, mutually opposed arms is interposed between the end portions of the interlocking member of the second one of the at least two, mutually opposed arms, and the connecting member of the second one of the at least two, mutually opposed arms is interposed between the end portions of the interlocking member of the first one of the at least two, mutually opposed arms.

2. The release mechanism as claimed in claim 1, wherein the actuating member comprises a substantially cylindrical, elongate member, and each interlocking member extends around more than 180° of the circumference of the actuating member when the actuating member is in the interlocking position.

3. The release mechanism as claimed in claim 1, wherein the mutually opposed arms comprises a pair of arms, each having a longitudinal axis and, when the actuating member is in the interlocking position, the longitudinal axes of the arms are substantially parallel to each other.

4. The release mechanism as claimed in claim 1, wherein each interlocking member comprises a strip joined at least at one end, and at either end, of the strip to the respective arm and depending therefrom in the general direction of an opposing arm wherein each strip and respective arm together extend circumferentially around the actuating member to prevent opening of the arms.

5. The release mechanism as claimed in claim 4, wherein each arm has a generally arcuate inner surface, and each strip is generally arcuate such that the arcuate strip and respective arm together at least partially, and entirely, encircle the actuating member when the actuating member is in the interlocking position.

6. The release mechanism as claimed in claim 4, wherein each strip is integrally formed with a respective arm.

7. The release mechanism as claimed in claim 4, wherein each strip is defined by a pair of circumferential slits in a generally concave portion of the respective arm, the strip between the pair of circumferential slits being deflected inwardly in the general direction of an opposing arm, by pressing on the strips, to form a generally convex arcuate strip.

8. The release mechanism as claimed in claim 1, wherein at least the arms or the elongate shaft are flexible, being formed from a flexible material, comprising a flexible polymeric material being polyimide.

9. The release mechanism as claimed in claim 1, wherein at least the arms or the elongate shaft comprise a flexible metal alloy, being formed from a flexible metal alloy.

10. The release mechanism as claimed in claim 1, wherein the arms are integrally formed with the elongate shaft.

11. The release mechanism as claimed in claim 1, wherein the arms are laser cut from the distal end of the elongate shaft.

12. The release mechanism as claimed in claim 1, wherein the actuating member comprises a wire, the wire being retractable from a proximal end of the elongate shaft to move the actuating member to the releasing position to release the arms.

13. The release mechanism as claimed in claim 1, wherein the hollow space at least partially defined by the gripping portions is configured for holding an embolic coil, an embolic coil having an enlarged head portion at a proximal end thereof, the head portion being substantially spherical.

14. The release mechanism as claimed in claim 1, wherein the gripping portions of the arms define the distal end of the release mechanism and have a dimension generally perpendicular to the longitudinal axis of the elongate shaft that is less than the outer diameter of the elongate shaft so as not to increase the outer profile of the release mechanism when the actuating member is in the interlocking position and the arms are closed.

15. A method of manufacturing a release mechanism for releasing a medical device, the method comprising:
    forming a hollow elongate shaft that defines a longitudinal axis; and
    cutting to form at least two, mutually opposed arms at a distal end thereof such that the arms are biased to open when unconstrained, each arm having at least one interlocking member; a gripping portion; and a connecting member,
    wherein the gripping portion located at the distal end of the arm, wherein the interlocking member of each arm is longitudinally spaced from the interlocking member of any other arm, the gripping portions are formed so as to at least partially define a hollow space for holding the medical device to be released, and the interlocking members are formed such that each interlocking member extends around a sufficient proportion of an actuating member receivable within the hollow elongate shaft such that opening of the arms is prevented by interaction between the actuating member and the interlocking members;
    wherein the connecting member of a first one of the at least two, mutually opposed arms is located generally opposite the interlocking member of a second one of the at least two, mutually opposed arms, and the connecting member of the second one of the at least two, mutually opposed arms is located generally opposite the interlocking member of the first one of the at least two, mutually opposed arms;
    wherein each interlocking member defines a spacing between end portions of the respective interlocking member, the connecting member of the first one of the at least two, mutually opposed arms is interposed between the end portions of the interlocking member of the second one of the at least two, mutually opposed arms, and the connecting member of the second one of the at least two, mutually opposed arms is interposed between the end portions of the interlocking member of the first one of the at least two, mutually opposed arms.

16. The method of claim 15, further comprising:
    cutting a first pair of circumferential slits into a first one of the at least two mutually opposed arms to define a first strip;
    cutting a second pair of circumferential slits into a second one of the at least two mutually opposed arms to define a second strip, the second strip being longitudinally spaced from the first strip; and
    pressing the first and second strips inwardly in the general direction of an opposing arm to form arcuate strips.

17. The method of claim 16, further comprising introducing an actuating member, comprising an actuating wire, into the lumen defined by each arcuate strip and the respective arm from which it is cut, thereby holding the arms against their bias to open.

18. A method of releasing a medical device at a release location within a body, comprising the steps of:
    gripping the medical device by a release mechanism comprising a generally elongate shaft defining a longitudinal axis and at least two, mutually opposed arms at a distal end of the elongate shaft, the arms being biased to open relative to each other and each comprising a gripping portion at a distal end thereof serving to grip the medical device, at least one interlocking member, and a connecting member;
    locking the release mechanism by positioning an actuating member such that the interlocking members extend circumferentially around a sufficient proportion of the actuating member to prevent opening of the arms;
    navigating the release mechanism to the release location; and retracting the actuating member longitudinally to enable the arms to open so releasing the medical device from the gripping portions;

wherein the connecting member of a first one of the at least two, mutually opposed arms is located generally opposite the interlocking member of a second one of the at least two, mutually opposed arms, and the connecting member of the second one of the at least two, mutually opposed arms is located generally opposite the interlocking member of the first one of the at least two, mutually opposed arms;

wherein each interlocking member defines a spacing between end portions of the respective interlocking member, the connecting member of the first one of the at least two, mutually opposed arms is interposed between the end portions of the interlocking member of the second one of the at least two, mutually opposed arms, and the connecting member of the second one of the at least two, mutually opposed arms is interposed between the end portions of the interlocking member of the first one of the at least two, mutually opposed arms.

\* \* \* \* \*